United States Patent
Sass

(10) Patent No.: US 6,792,316 B2
(45) Date of Patent: Sep. 14, 2004

(54) CARDIAC IMPLANT CABLE HAVING A COAXIAL LEAD

(75) Inventor: Richard G. Sass, Portland, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 136 days.

(21) Appl. No.: 10/038,560

(22) Filed: Jan. 3, 2002

(65) Prior Publication Data

US 2002/0058978 A1 May 16, 2002

Related U.S. Application Data

(62) Division of application No. 09/415,534, filed on Oct. 8, 1999, now Pat. No. 6,374,141.

(51) Int. Cl.⁷ ................................................. A61M 1/05
(52) U.S. Cl. ....................... 607/116; 600/373; 600/374; 607/119
(58) Field of Search ................................. 607/116–129; 600/372–381

(56) References Cited

U.S. PATENT DOCUMENTS

| | | | | |
|---|---|---|---|---|
| 4,840,186 A | * | 6/1989 | Lekholm et al. | 607/116 |
| 4,945,342 A | * | 7/1990 | Steinemann | 174/113 R |
| 5,954,760 A | * | 9/1999 | Jarl | 607/122 |
| 6,004,269 A | * | 12/1999 | Crowley et al. | 600/439 |
| 6,434,430 B2 | * | 8/2002 | Borgersen et al. | 607/122 |

* cited by examiner

Primary Examiner—Jeffrey R. Jastrzab
(74) Attorney, Agent, or Firm—Law Office of Timothy E. Siegel; Timothy E. Siegel

(57) ABSTRACT

A cardiac implant electric cable, comprising a conductive lead adapted to supply power to a cardiac implant and a coaxial lead adapted to provide an expanded information conduit to and from said cardiac implant. Also, a bioelectrical stimulus implant cable may comprise a set of fibrils, each of which has a diameter of less than 30 μm and which are configured together longitudinally. The set of fibrils is electrically isolated by insulative material.

7 Claims, 5 Drawing Sheets

US 6,792,316 B2

CARDIAC IMPLANT CABLE HAVING A COAXIAL LEAD

RELATED PATENT APPLICATIONS

The present application is a divisional of U.S. patent application Ser. No. 09/415,534 now U.S. Pat. No. 6,374,141, filed Oct. 8, 1999.

BACKGROUND OF THE INVENTION

The present invention is a bioelectrical stimulus implant cable that has improved durability and signal carrying capabilities over currently available bioelectrical stimulus implant cables.

Bioelectrical stimulus implant cables include cardiac implant cables, neuro-stimulus cables and any cable designed to apply an electric charge to body tissue or to supply a device which applies such a charge.

Bioelectrical stimulus implant cables must meet a number of challenging criteria. For example, a cardiac implant cable typically stretches from a subcutaneous fat deposit through the rib cage to a cardiac implant such as a pacemaker. The cable is continuously perturbed by the beating of the heart. It must not, however, become fatigued by this constant flexure to the point where a substantial number of the cable fibrils break. (A fibril is a thin wire used in a cable.) Not only does a broken fibril not conduct electricity to the implant but it also may work its way through the insulating layers of the cable and make harmful contact with body tissue. A bioelectrical stimulus cable must also be completely biocompatible. That is, the exterior of the cable must be made of biocompatible materials and the constant flexure caused by movement of the patient or his organs must not cause a rupture that would lead to the release of materials that are not biocompatible.

Heretofore, the general approach to the production of this type of cable has been to produce a tight helix so each fibril would experience only a small part of the total cable flexure. One problem with a tight helix is that it places a restriction on the number of independent leads that can be included in the cable. If more leads could be included in a cable, however, more purposes could be served with respect to an implant. For example, a single cardiac implant may function as both a pacemaker and as a defibrillator and may require a set of leads to power the pacemaker and a separate set of leads to power the defibrillator when it is needed. Additionally, a set of control leads may be necessary to, for example, adjust the operation of the pacemaker and the defibrillator.

Another problem encountered in the use of bioelectrical stimulus cables is the formation of scar tissue about the cable. It is occasionally necessary to replace a bioelectrical stimulus cable. Removing the old cable can provide a difficult challenge to the surgeon performing the replacement if considerable scar tissue has grown about and adhered itself to the cable, as is typical.

SUMMARY OF THE INVENTION

In a first separate preferred aspect the present invention is a cardiac implant electric cable, comprising a conductive lead adapted to supply power to a cardiac implant and a coaxial lead adapted to provide an expanded information conduit to and from said cardiac implant.

In a second separate preferred aspect the present invention is a bioelectrical stimulus implant cable that comprises a set of fibrils, each of which has a diameter of less than 30 μm and which are configured together longitudinally. The set of fibrils is electrically isolated by insulative material.

The foregoing and other objectives, features, and advantages of the invention will be more readily understood upon consideration of the following detailed description of the invention, taken in conjunction with the accompanying drawings.

DETAILED DESCRIPTION OF THE PREFERRED EMBODIMENT

Figure 1:
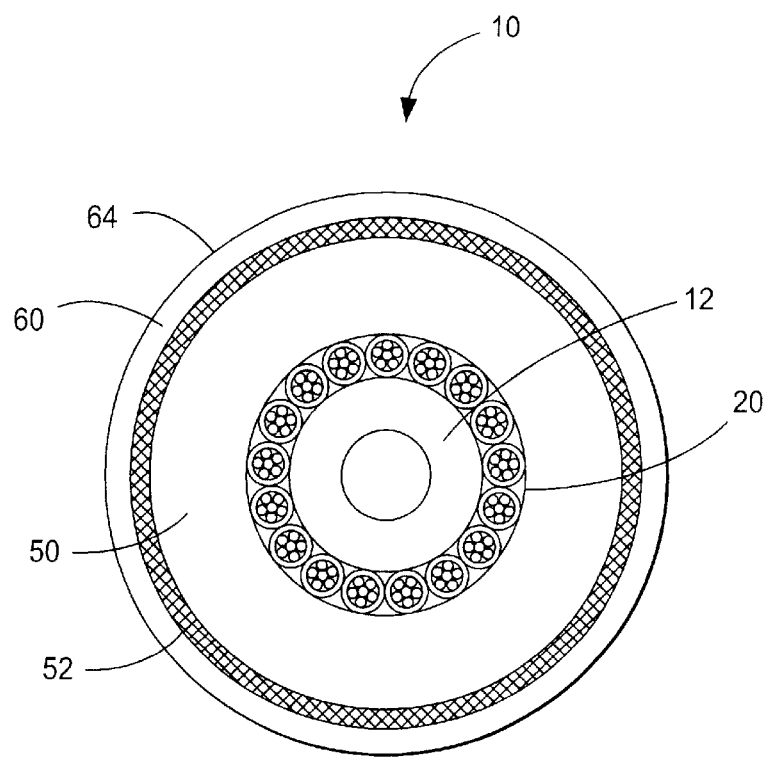
FIG. 1 is a greatly expanded transverse cross-sectional view of a bioelectrical stimulus cable according to the present invention.
Figure 2:
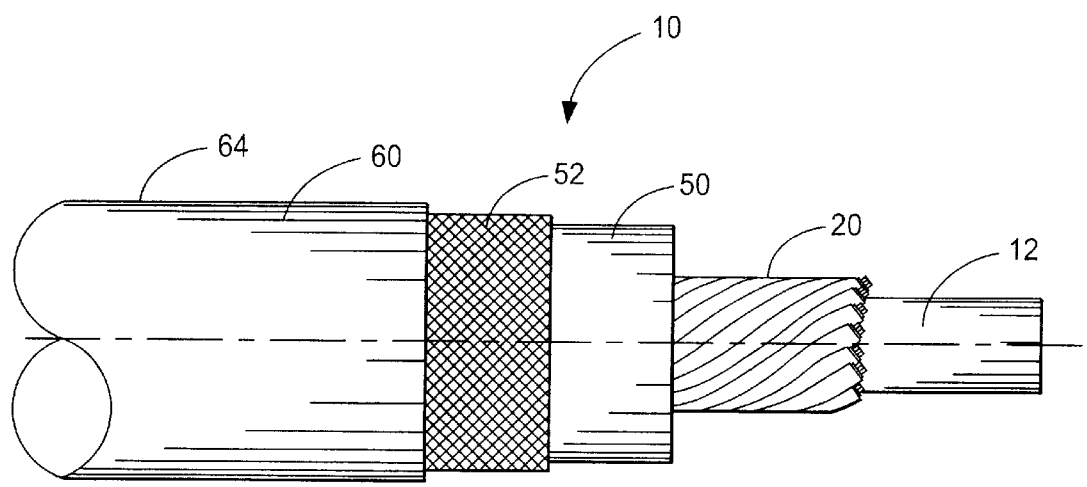
FIG. 2 is a greatly expanded longitudinal cutaway view of the bioelectrical stimulus cable of FIG. 1.

Referring to FIGS. 1 and 2, a preferred embodiment of a bioelectrical stimulus cable 10 according to the present invention has a diameter of 3 mm (119 mils). At its center is a central lumen 12 preferably made of polyurethane or silicone and having an inner diameter of 0.45 mm (0.018") and an outer diameter of 0.96 mm (0.038"). The central lumen 12 performs at least two important functions. First, it may accommodate a guide wire during the insertion process. Second, it adds rigidity to the cable.

Arranged about central lumen 12 are thirteen insulated leads 20, each having a diameter of 0.22 mm (0.0087"). In an alternative embodiment fillers, each also having a diameter of 0.22 mm (0.0087"), are interspersed with a reduced number of leads 20. Referring to FIG. 2, the leads 20 are wrapped about central lumen 12 in a "lazy" helix having a lay length of between 10 mm (0.4") and 15 mm (0.6"). Such an arrangement is necessary when so many leads are used, thirteen leads being considerably more than is typically available in prior art cables.

Figure 6:
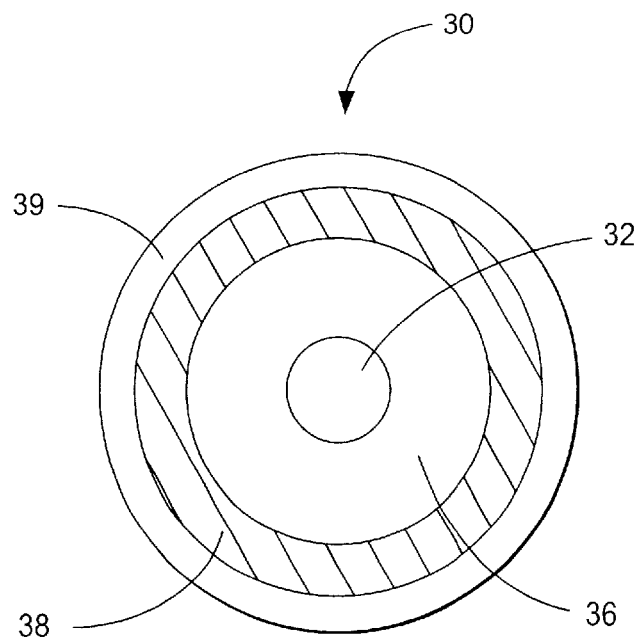
FIG. 6 is a still more greatly expanded cross-sectional view of a single coaxial lead of the bioelectrical stimulus cable of FIG. 4.
Figure 4:
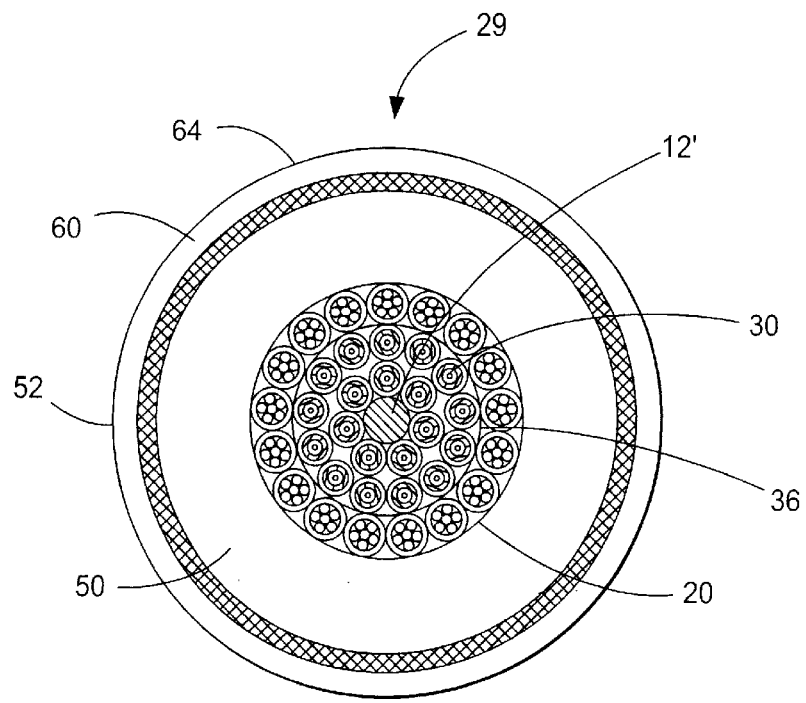
FIG. 4 is a greatly expanded transverse cross-sectional view of an alternative preferred embodiment of a bioelectrical stimulus cable according to the present invention.
Figure 5:
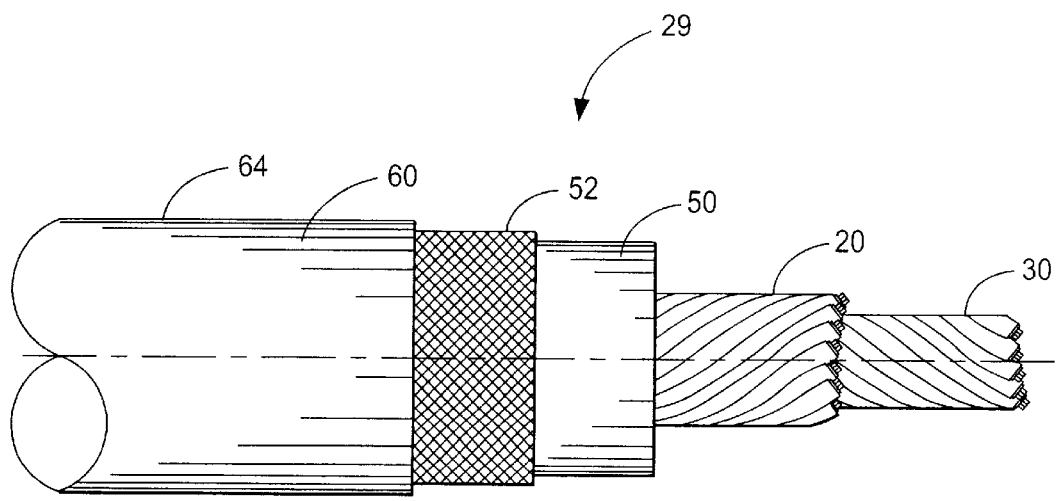
FIG. 5 is a greatly expanded longitudinal cutaway view of the bioelectrical stimulus cable of FIG. 3.

FIGS. 4, 5 and 6 show an alternative embodiment 29 having a central filler 12' rather than tube 12 and twenty coaxial insulated leads 30 twisted counter to leads 20. Each coaxial lead 30 has a central conductor 32 that is 40 μm in diameter and is made from four 20 μm (0.8 mil) strands of silver plated CS95, available from Phelps Dodge of Inman, S.C., that have been stranded and twisted together. Central conductor 32 is covered with a 38 μm (1.5 mil) thick coating 36 of fluorinated ethylene propylene (FEP). This, in turn, is covered with a shield 38 made of 20 μm (0.8 mil) strands of CS95 that collectively provide 90% minimum coverage. A 13 μm (0.5 mil) wall 39 of polyurethane surround the coaxial lead 30, which has a 50 ohm impedance. The provision of coaxial leads 30 permits a far greater total bandwidth for the transmission of instrumentation data than is currently available in bioelectrical stimulus leads.

Figure 3:
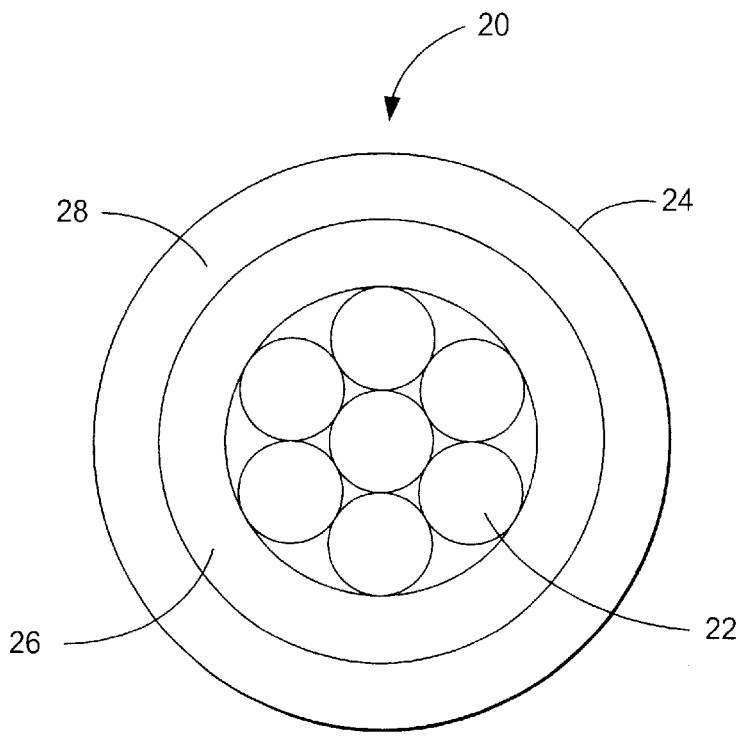
FIG. 3 is a still more greatly expanded cross-sectional view of a single insulated lead of the bioelectrical stimulus cable of FIG. 1.

Referring to FIG. 3, each of the insulated leads 20, includes seven strands or fibrils 22, each of which is a 40 μm (1.57 mil) strand of MP35N, an alloy that is frequently used in cardiac cables due to its durability and biocompatibility. MP35N is widely available from several different suppliers. Alternatively, one of the fibrils 22 is a drawn filled tube (DFT) with walls of MP35N filled with silver. Immediately surrounding each group of fibrils 22 is a bimaterial coat 24, having an interior coating 26 that is 25.4 μm (1 mil) thick and is made of ethylene tetrafluoroethylene (ETFE). An outer elastomeric coating 28 of coat 24 is 25.4 μm (1 mil) thick and may be made of polyurethane. Because ETFE has a higher melting temperature than polyurethane, ETFE interior coating 26 may be coated with melted polyurethane, without melting any of the ETFE.

Figure 7:
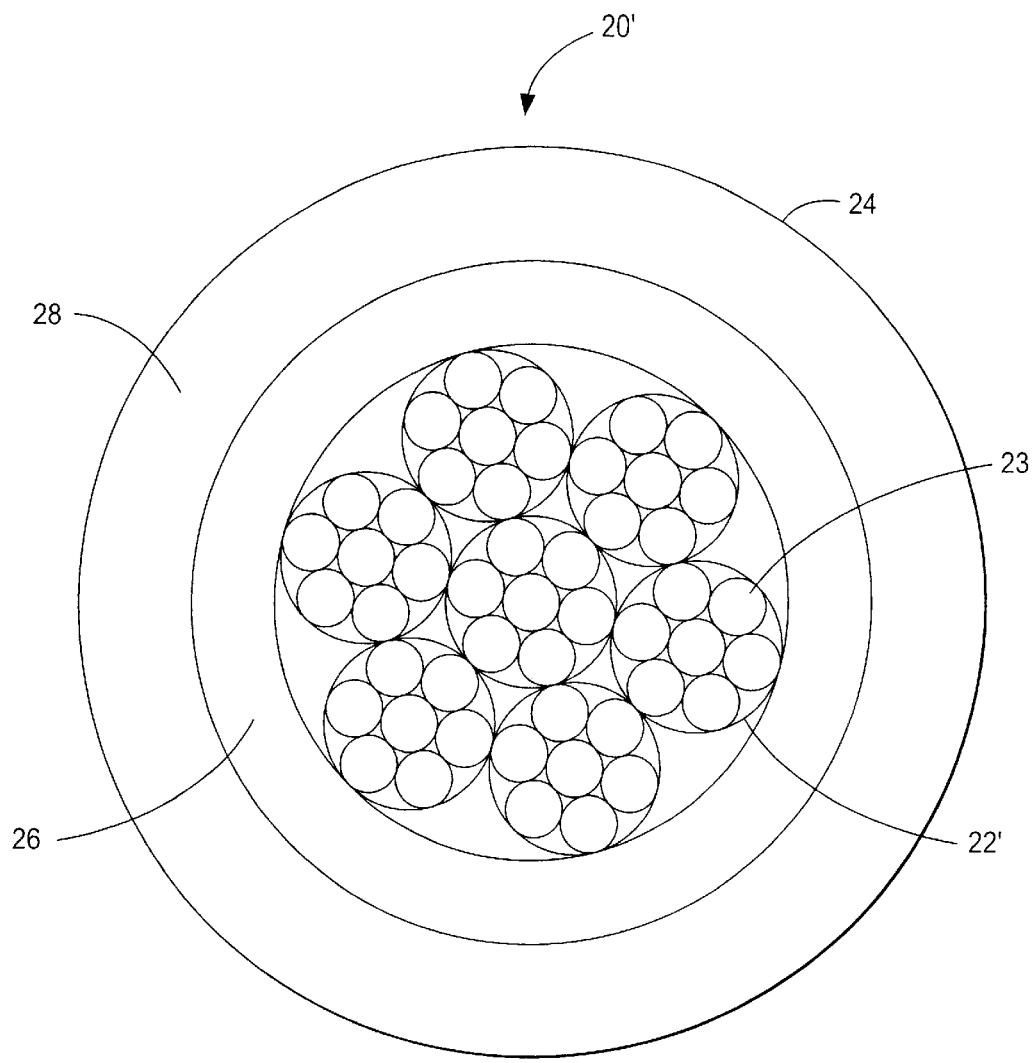
FIG. 7 is a still more greatly expanded cross-sectional view of a single insulated lead of a bioelectrical stimulus cable identical with that of FIG. 1 except that it includes the insulated leads shown in FIG. 7.

Referring to FIG. 7, an alternative preferred embodiment includes leads 20', in place of leads 20. Each lead 20' is made of seven strands 21' of 12.7 μm (0.5 mil) thick fibrils 23 of MP35N. Lead 20' is even more resilient and wear resistant than lead 20. The use of the smaller diameter fibrils imparts superior physical characteristics to cable 20' due to the inherently greater flexibility and freedom from incusions of these fibrils 23.

Coat 24 is an important part of the present invention. The principal problem that should be avoided in cardiac cables is that of fibrils 22 breaking from extended fatigue. The breaking of a fibril, however, does not typically occur in a single undifferentiated step. Rather, the fibril first develops a sharp bend or kink through extended wear. After the kink is formed a break typically occurs fairly rapidly. If a fibril does not kink it is far less likely to ever break. ETFE is a rigid material that holds the fibrils so that they remain straight and unbent. ETFE is also a low friction material, so that each set of fibrils 22 may slide with respect to the interior surface of coating 26, thereby avoiding internal strain. Elastomeric coating 28 provides cushioning between neighboring leads 20 and helps to prevent fibril kinking and fatigue by absorbing the shock caused by the heart beats.

Surrounding insulated leads 20 is a 500 μm (0.02") tubular wall 50 of elastomeric insulating material, such as silicone or polyurethane. Wall 50 is elastomeric or spongy enough to dampen the vibrations caused by the beating of the heart yet thick and substantial enough to help prevent kinking of the fibrils 22. Outside of wall 50 is a 100 μm (0.004") tubular polyester fiber braid 52. This braid imparts tensile strength to cable 10 not only because of its own tensile strength but also because when it is pulled it contracts radially, squeezing the interior portions of cable 10 and thereby increasing the overall tensile strength of cable 10.

Finally, at the radial exterior of cable 10 is a 127 μm (0.005") polyurethane or silicone wall 60. Preferably, this wall is made of polyurethane with TFE end groups, to create a low friction surface. A low friction surface 64 may be helpful when removing cable 10 from a patient as is sometimes necessary. In addition, the surface 64 may be ribbed or otherwise textured with a 10 micron order of magnitude three dimensional structure designed to encourage healthy tissue growth about the cable and to prevent the growth of scar tissue. Interlinked holes within the range of 2–150 microns in diameter have been found to be an effective structure for encouraging the growth of healthy tissue. In one preferred embodiment surface 64 is textured with interlinked holes in this size range. In an additional preferred embodiment the radially outermost portion of cable 10 is separable from the portion containing the leads 20, so that the lead containing portion may be replaced without removing surface 64 which may be retained by body tissue.

Figure 8:
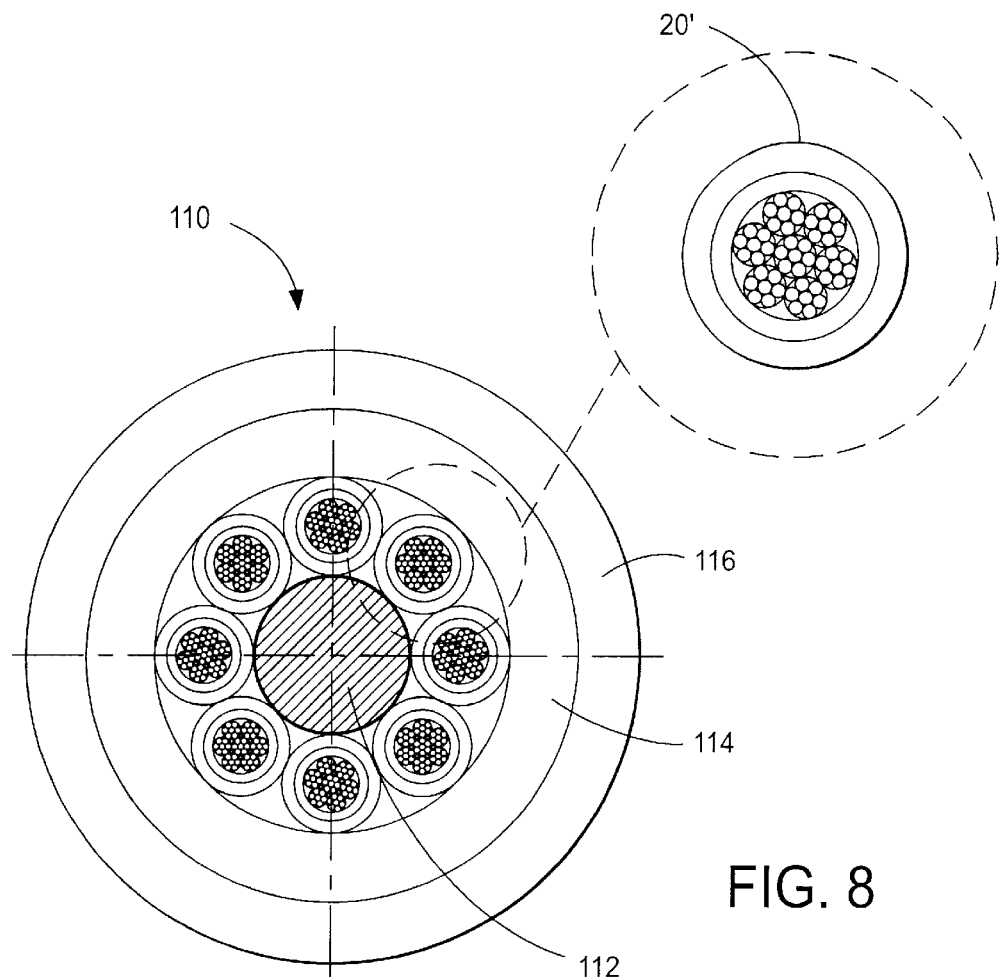
FIG. 8 is a greatly expanded transverse cross-sectional view of a cable for treating congestive heart failure.
Figure 9:
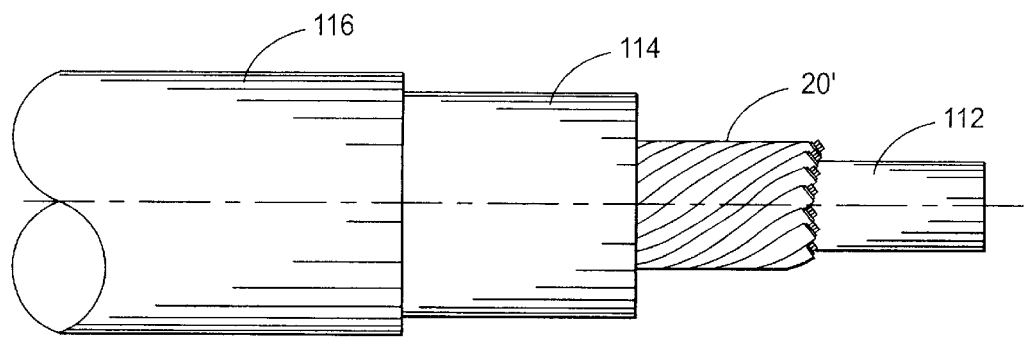
FIG. 9 is a greatly expanded longitudinal cutaway view of the cable of FIG. 8.

Referring to FIGS. 8 and 9 a bioelectrical stimulus cable 110 designed for the treatment of congestive heart failure includes eight insulated leads 20' (shown in greater detail in FIG. 7), each of which can be used either for the transmission of power or for the transmission of sensor data or control data. In the treatment of congestive heart failure it is typically desirable to stimulate the heart at a number of different sites. The presence of eight leads, each of which could be used for power transmission in cable 110, permits flexibility in meeting these requirements.

Leads 20' are wound helically about a central silicone rod 112 that has a diameter of 333 μm (13 mils). Surrounding leads 20' is a tube of silicone having a wall thickness of 0.33 mm (13 mils). Exterior to this tube is another tube 116 having a wall thickness of 127 μm (5 mils) being made of 80% polyurethane and 20% silicone. The entire cable 110 has a diameter of 1.651 mm (65 mils) as opposed to 3 mm for cable 10. This reduced diameter is desirable in a cable for the treatment of congestive heart failure.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A living body implantable electric cable comprising:

(a) a plurality of conductive leads, each conductive lead adapted to supply power to a living body implant; and (b) a plurality of coaxial leads, each separate from said conductive leads and made of a central conductor, a dielectric layer that is substantially conformal to said central conductor and a conductive shield, said coaxial leads being adapted to provide an expanded information conduit to or from said living body implant.

2. The living body implantable electrical cable of claim 1, wherein said central conductor is less than 80 μm in diameter.

3. The living body implantable electrical cable of claim 1, wherein said dielectric layer forms a tube having an inner diameter of less than 90 μm.

4. The living body implantable electrical cable of claim 1, more specifically being a human body implantable electrical cable.

5. The living body implantable electrical cable of claim 1, more specifically being an animal body implantable electrical cable.

6. A bioelectrical stimulus cable, comprising:

(a) a set of fibrils, each having a diameter of less than 30 μm and being stranded together and wherein separate subsets of said fibrils are stranded together into separate stranded subsets and wherein said stranded subsets are stranded together into a stranded set of stranded subsets; and (b) insulative material electrically isolating said set of fibrils.

7. The bioelectrical stimulus cable of claim 6 wherein said fibrils each have a diameter of less than 20 μm.

* * * * *